United States Patent [19]
Cornell et al.

[11] Patent Number: 5,486,205
[45] Date of Patent: Jan. 23, 1996

[54] DIFFUSED AIR HEATING SYSTEM

[75] Inventors: Jeffrey L. Cornell, Coldwater; Thomas H. Phlipot, Jackson, both of Mich.

[73] Assignee: Progressive Dynamics, Inc., Marshall, Mich.

[21] Appl. No.: 229,382

[22] Filed: Apr. 18, 1994

[51] Int. Cl.⁶ .................................................. A61F 7/00
[52] U.S. Cl. ........................... 607/104; 219/527; 219/530
[58] Field of Search .................. 607/96, 104, 107–108; 219/487, 489–490, 412, 530, 527–528, 212, 482; 165/46

[56] References Cited

U.S. PATENT DOCUMENTS 3,894,213  7/1975  Agarwala ............................ 607/104 X
5,300,098  4/1994  Philipot ................................. 607/96

*Primary Examiner*—Angela D. Sykes
*Attorney, Agent, or Firm*—Beaman & Beaman

[57] ABSTRACT

An air diffuser system for a medical thermal blanket wherein air forced over an elongated heat exchanger is substantially uniformly distributed over the heat exchanger and a thermal sensor located downstream over the heat exchanger to eliminate localized hot and cold "spots" and permit accurate temperature measurement of the air and provide an effective exchange of heat between flowing air and the heat exchanger, the apparatus of invention is characterized by its concise configuration and dimensions.

15 Claims, 1 Drawing Sheet

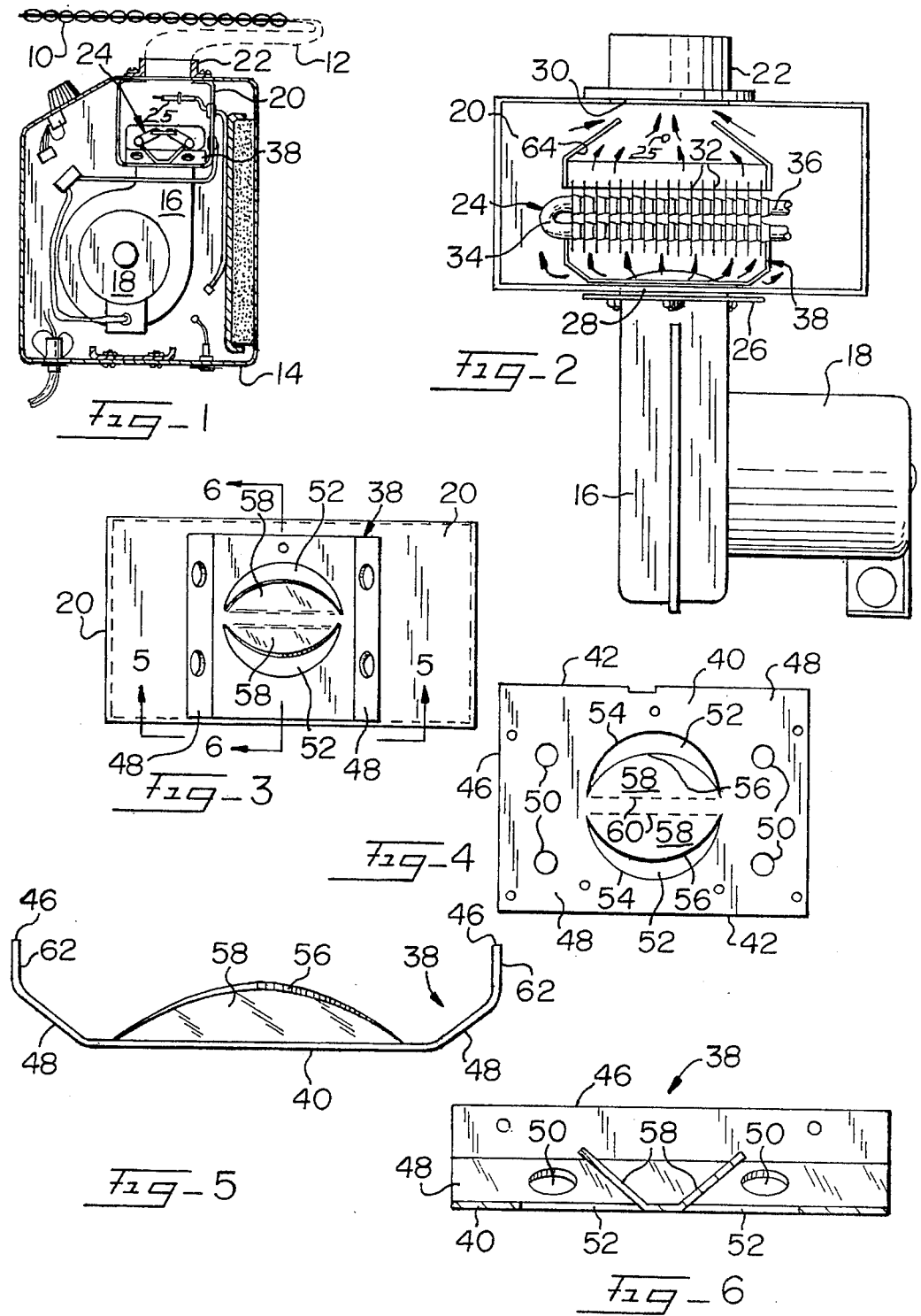

5,486,205

DIFFUSED AIR HEATING SYSTEM

BACKGROUND OF THE INVENTION

1. Field of the Invention

The invention pertains to a concise air diffuser system particularly suitable for use with medical thermal blankets wherein the temperature of forced air is controlled by passing the air over a heat exchanger.

2. Description of the Related Art

In the assignee's U.S. Pat. No. 5,125,238 and the assignee's U.S. Pat. No. 5,300,098, a medical thermal blanket, and controls, are disclosed wherein temperature controlled air, usually heated air, is forced into an inflatable blanket having a plurality of orifices whereby the heated air impinges upon a patient to maintain or increase body temperature. Such blankets are often used in post surgery and trauma situations.

Because of the nature of a medical thermal blanket, i.e. the apparatus must be of concise configuration as to be readily portable as placed bedside, the space available for heating the air prior to introduction into the blanket is limited, and it is necessary to effectively transfer heat from air forced by a fan into a heat exchanger containing plenum. The heat exchanger, of the heating type, is of the electrical resistance format, and in order to provide maximum heat exchanger life it is important that a uniform flow of forced air pass over the heat exchanger to prevent localized hot or cold spots on the heat exchanger, efficiently transfer the heat from the heat exchanger to the air, and provide a uniformly heated air to the blanket. Also, in order to provide accurate temperatue control, the temperature of the air flowing over the thermal sensor downstream of the heat exchanger must be substantially equivalent to the uniformly heated air supplied to the blanket.

Diffusers for heated air often take the form of louvers or vanes, such as shown in U.S. Pat. Nos. 1,879,152; 2,241,753; 2,699,323 and 4,176,709. However, conventional air diffusers used in conjunction with heat exchangers of the aforementioned type are not suitable for use with concisely related heat exchangers employing a closed plenum, and prior to the advent of the instant invention an efficient and concise air/heat exchanger system using an air diffuser has not been available.

OBJECTS OF THE INVENTION

It is an object of the invention to provide a concise diffuser system for use with a medical thermal blanket wherein air forced into a plenum containing a heat exchanger and thermal sensor is uniformly distributed over the heat exchanger and sensor with a minimum loss of pressure and a minimum of resistance to air flow.

A further object of the invention is to provide an air diffuser system for use with a medical thermal blanket wherein the diffuser requires no moving parts, quietly diffuses the air evenly over the heat exchanger and thermal sensor, and is of an economical manufacture.

Yet another object of the invention is to provide a diffuser system for a medical thermal blanket utilizing an elongated heat exchanger wherein the diffuser distributes the air in an elongated pattern along the length of the heat exchanger to assure uniform heat exchanging characteristics and prevent localized excessive heating or cooling heat exchanger problems.

An additional object of the invention is to provide a concise diffuser system for use with a medical thermal blanket wherein a heat exchanger is located within a plenumand a thermal temperature sensor is located downstream from the heat exchanger wherein an accurate air temperature measurement at the location of the thermal sensor represents the air temperature downstream of the heat exchanger which is supplied to the blanket.

SUMMARY OF THE INVENTION

A medical blanket system using the diffuser system of the invention receives temperature controlled air pressurized by a fan. Usually, the pressurized air is heated by an electrically operated heat exchanger wherein the pressurized air supplied to the blanket has been heated to a pre-determined temperature. The fan is located within a housing, and a heat exchanger plenum is located within the housing and receives the pressurized air supplied by the fan. The heat exchanger is located within the plenum, and the plenum includes an outlet communicating with the blanket through a flexible hose.

The heat exchanger is of an elongated configuration using a plurality of fins heated by the heat exchanger core, and air discharged from the fan passes over the heat exchanger and fins absorbing heat therefrom for discharge from the plenum to supply the blanket. The diffuser .system of the invention is located adjacent the plenum pressurized air inlet whereby the air entering the plenum immediately engages the diffuser and is spread over the heat exchanger length in such a manner as to eliminate localized hot or cold "spots" on and downstream of the heat exchanger resulting in a substantially uniformly heated air which passes across the thermal sensor and through the plenum outlet to the blanket supply hose.

The diffuser system consists of a pair of arc or crescent shaped openings defined by a planar diffuser base and a deflector bent from the base. The resulting diffuser opening is of a somewhat elongated configuration having a greater dimension at the central region of the opening than at the opening ends. The angle of the diffuser, and its location, with respect to the plenum inlet results in a substantially uniform flow of air over the length of the heat exchanger resulting in an efficient transfer of heat to the air. The construction of the diffuser system provides highly efficient and effective air diffusion in a concise configuration.

The diffuser system also includes vent holes whereby a portion of the pressurized air passes over the end regions of the heat exchanger to prevent overheating thereof.

The diffuser is economically formed by a sheet metal stamping and bending processes, and may be readily fabricated using known manufacturing techniques.

BRIEF DESCRIPTION OF THE DRAWINGS

The aforementioned objects and advantages of the invention will be appreciated from the following description and accompanying drawings wherein:

FIG. 1 is an elevational sectional view through the control housing for a thermal medical blanket illustrating the heat exchanger plenum therein, FIG. 2 is an enlarged elevational view, partially sectioned, illustrating the fan and heat exchanger plenum, FIG. 3 is a plan view of the plenum and diffuser, the heat exchanger being eliminated for purpose of illustration, FIG. 4 is a view of the diffuser blank after the openings have been stamped, and prior to bending of the blank lateral regions, FIG. 5 is an elevational end view of the diffuser as taken along Section 5—5 of FIG. 3, and FIG. 6 is a sectional view through the diffuser as taken along Section 6—6 of FIG. 3.

DESCRIPTION OF THE PREFERRED EMBODIMENT

With reference to FIG. 1, a thermal medical blanket is illustrated at 10 which will be of the general type shown in the assignee's U.S. Pat. No. 5,125,238. The blanket 10 is inflatable by forced air and is placed over the patient's body and includes openings whereby the temperature controlled air within the blanket is directed over the patient. The air inflating the blanket 10 is provided through a flexible supply hose 12 shown in dotted lines. The blanket system includes a housing 14 upon which the controls are located, and the housing 14 internally includes a centrifugal fan 16 powered by an electric motor 18. A plenum 20 is located within the housing 14 defining a separate chamber therein, and the hose fitting 22 is exteriorly mounted upon the upper region of the housing 14 for connection with the hose 12. An electric heat exchanger 24 is located within the plenum 20, and a mounting plate 26 may be used to mount the plenum upon the outlet of the fan 16. The plenum 20 includes an inlet 28 communicating with the outlet of fan 16, and the plenum 20 also includes an outlet 30 which is in direct communication with the hose fitting 22 as will be appreciated from FIG. 2. A thermal sensor 25 is mounted in the plenum 20 downstream of heat exchanger 24 between the heat exchanger 24 and hose fitting 22 to permit control of the heating circuit as explained in U.S. Pat. No. 5,300,098.

The heat exchanger 24 is of an elongated configuration and is preferably of the electric resistance type having a plurality of plates 32 mounted thereon constituting fins which are in a heat conducting relationship to the heat exchanger core, and are surrounded by air within the plenum 20. The end regions of the heater are represented at 34 and 36, respectively, the end 34 constituting a hairpin type 180° turn. The heat exchanger 24 is of a conventional commercial type and its construction, per se, constitutes no inventive aspect to the present invention.

The diffuser 38 is located within the plenum 20 adjacent the plenum inlet 28. The diffuser 38 may have mounting tabs extending through the plenum and may be bolted to the mounting plate 26.

The diffuser 38 is of a sheet metal construction and is preferably formed of a flat sheet metal blank, FIG. 4, the sheet metal blank basically consisting of a base 40 of a planar configuration. The blank includes an upper edge 42 and a lower edge 44, and lateral edges 46. The blank includes lateral regions 48 adjacent the edges 46, and vent holes 50 are formed in the lateral regions 48.

The primary air flow through the diffuser 38 is through the openings 52, two of which exist, and are of identical configuration. The openings 52 each include an outer circular arc 54 and an inner circular arc 56 wherein portions 58 are formed in the diffuser blank adjacent the arcs 56.

The portions 58 constitute deflectors as the portions 58 are bent inwardly approximately 40° with respect to the plane of the base 40, FIG. 6, and the deflectors 58 each define an opening 52 by the associated arcs 54 and 56. Accordingly, the openings 52 are of a maximum area at their central region, and at a minimum area where the arcs 54 and 56 intersect. In a commercial embodiment of the invention, the radius of the arcs 56 is 1.320 inches, while the radius of the opening arcs 54 is 1.188 inches, and the greater radius of the arcs 56 permits a configuration of opening 52 which provides the desired air diffusion and distribution. The dotted lines 60, FIG. 4, represent the bend or hinge lines of the deflectors 58.

As will be appreciated from FIGS. 5 and 6, the lateral regions 48 of the diffuser blank are bent upwardly 37° from the plane of the base 40, and the baffle end portions 62 immediately adjacent the lateral edges 46 are further bent to a vertical orientation as will be appreciated from FIG. 5.

The diffuser 38 is oriented to the heat exchanger 24 in a manner as will be appreciated from FIGS. 1 and 2, wherein the length of the openings 52 is disposed parallel to the length of the heat exchanger 24. Accordingly, the air passing through the diffuser openings 52 will be distributed along the length of the heat exchanger, and the air will pass over the heat exchanger fins 32 wherein the air will absorb heat therefrom and the diffused air also passes over thermal sensor 25.

Air entering the diffuser through the openings 52, to a limited extent, will also flow through the vent holes 50 defined in the lateral regions 48, and this air will pass over the heat exchanger ends 34 and 36 keeping the ends of the heat exchanger from overheating. However, it will be understood that the majority of the air being diffused by the openings 52 passes over the heat exchanger plates 32.

An upper baffle 64 is located within the plenum 20 above the heat exchanger 24, and includes upwardly converging walls extending towards the hose fitting 22 and plenum outlet 30. The upper ends of the baffle 64 terminates short of the upper surface of the plenum 20 whereby air flowing through the vent holes 50 will enter the hose fitting 22, and the mixture of the forced air being blown through the openings 52, and vent holes 50, produces a well diffused flow of air over the thermal sensor 25 and into the hose fitting 22 of even temperature throughout the area of the hose fitting and thermal sensor assuring an evenly heated distribution of air within the hose 12 as discharged into the blanket 10 and assuring accurate air temperature sensing.

The configuration of the openings 52, and the use of the deflectors 58, produces a flow of air over the heat exchanger 24 creating considerable turbulence as to produce the desired mixture of air to reduce hot or cold "spots" upon the heat exchanger 24, its fins 32 and the air column above the heat exchanger 24. The diffuser 38 is of a concise configuration readily receivable within the plenum 20, and as the diffuser is formed of sheet metal by a stamping operation a high strength is achieved at minimum fabrication costs.

It is appreciated that various modifications to the inventive concepts may be apparent to those skilled in the art without departing from the spirit and scope of the invention.

We claim:

1. An air diffuser system for a medical thermal blanket comprising, in combination, a plenum having an air inlet having an axis and an outlet, an elongated heat exchanger within said plenum in alignment with said inlet axis, an air diffuser located within said plenum in alignment with said inlet axis located intermediate said inlet and said heat exchanger receiving air discharged into said plenum from said inlet, said diffuser including an elongated opening having a length and a width, said opening length being substantially parallel to the length of said heat exchanger and of such configuration as to diffuse air received from said inlet substantially uniformly throughout the length of said heat exchanger.

2. In an air diffuser system for a medical thermal blanket as in claim 1, said diffuser opening including a deflector obliquely related to said air inlet axis.

3. In an air diffuser system for a medical thermal blanket as in claim 1, said diffuser opening having an arc configuration when projected parallel to said inlet axis.

4. In an air diffuser system for a medical thermal blanket as in claim 1, a deflector mounted on said diffuser obliquely disposed to said inlet axis and located adjacent said opening, said deflector having an outer periphery partially defining said diffuser opening.

5. In an air diffuser system for a medical thermal blanket as in claim 4, a pair of elongated openings defined in said diffuser, a pair of deflectors mounted on said diffuser each obliquely disposed to said inlet axis, and each located adjacent a diffuser opening, each deflector having an outer periphery partially defining the associated diffuser opening.

6. In an air diffuser system for a medical thermal blanket as in claim 4, said deflector outer periphery having an arcuate convex configuration.

7. In an air diffuser system for a medical thermal blanket as in claim 6, said deflector outer periphery comprising an arc of a circle.

8. In an air diffuser system for a medical thermal blanket as in claim 3, said diffuser opening being defined by inner and outer circular intersecting edges each having a different center of generation.

9. In an air diffuser system for a medical thermal blanket as in claim 8, the radius of said inner opening edge being slightly greater than the radius of said outer opening edge.

10. In an air diffuser system for a medical thermal blanket as in claim 2, said diffuser comprising a plate having a planar central base and opposed lateral portions, said opening and deflector being defined in said central base, said lateral portions being obliquely related to said central base, and air bypass vents defined in said lateral portions.

11. An air diffuser system for a medical thermal blanket comprising, in combination, a plenum having an air inlet having an axis and an outlet, an elongated heat exchanger within said plenum in alignment with said inlet axis, an air diffuser plate having a planar central base and spaced opposed lateral portions mounted within said plenum between said inlet and said heat exchanger, at least one elongated arc shaped opening defined in said central base in alignment with said inlet axis having a length substantially parallel to the length of said heat exchanger, and a deflector defined on said central base in alignment with said inlet axis and obliquely related thereto adjacent said opening diffusing air received from said inlet and passing through said opening over said heat exchanger.

12. In an air diffuser system for a medical thermal blanket as in claim 11, a pair of arc shaped openings defined in said central base in alignment with said inlet axis each having a length substantially parallel to the length of said heat exchanger, a deflector being associated with each opening.

13. In an air diffuser system for a medical thermal blanket as in claim 11, said opening having an outer periphery, said opening outer periphery constituting a segment of a circle.

14. In an air diffuser system for a medical thermal blanket as in claim 13, said deflector having an outer convex periphery constituting an arc of a circle.

15. In an air diffuser system for a medical thermal blanket as in claim 11, said lateral portions being obliquely related to said central base, and a plurality of air bypass vents defined in said lateral portions.

\* \* \* \* \*